(12) United States Patent
Pickering et al.

(10) Patent No.: US 6,168,567 B1
(45) Date of Patent: Jan. 2, 2001

(54) HYBRID SPHYGMOMANOMETER

(75) Inventors: Thomas G. Pickering, New York; John Holland, Lake Hill; William Pickering; Stephen Nicholas Weiss, both of Brooklyn, all of NY (US)

(73) Assignee: Accusphyg, LLC, Wingdale, NY (US)

( * ) Notice: Under 35 U.S.C. 154(b), the term of this patent shall be extended for 0 days.

(21) Appl. No.: 09/275,595

(22) Filed: Mar. 24, 1999

Related U.S. Application Data (63) Continuation-in-part of application No. 09/112,502, filed on Jul. 9, 1998, now abandoned, which is a continuation-in-part of application No. 09/265,734, filed on Mar. 10, 1999, now abandoned.

(51) Int. Cl.$^7$ .......................................... A61B 5/00
(52) U.S. Cl. ........................ 600/490; 600/493; 600/494
(58) Field of Search ............................... 600/490, 493.6, 600/500, 503

(56) References Cited

U.S. PATENT DOCUMENTS

| | | | |
|---|---|---|---|
| 3,319,623 | 5/1967 | London | 128/2.05 |
| 3,738,357 * | 6/1973 | Hayes | 600/498 |
| 4,320,767 | 3/1982 | Villa-Real | 128/680 |
| 4,343,314 | 8/1982 | Sramek | 128/680 |
| 5,201,320 * | 4/1993 | Barker et al. | 600/490 |
| 5,464,017 * | 11/1995 | Juang | 600/490 |
| 5,467,772 * | 11/1995 | Souma | 600/493 |
| 5,727,560 * | 3/1998 | Ogura | 600/494 |
| 5,997,476 * | 12/1999 | Brown | 600/300 |

* cited by examiner

Primary Examiner—Robert L. Nasser
(74) Attorney, Agent, or Firm—Milde, Hoffberg & Macklin, LLP

(57) ABSTRACT

A hybrid sphygmomanometer comprises:
(a) an arm cuff with an inflatable air bladder;
(b) a pumping device for inflating the air bladder;
(c) a manually controlled air outlet valve for deflating the air bladder;
(d) an air pressure transducer operative to receive the pressure in the air bladder of the arm cuff and to produce an electrical signal representing this pressure;
(e) a manually operated switch for generating systolic and diastolic interrupt signals;
(f) a first electronic display for displaying the instantaneous pressure in the air bladder in the form of a bar graph;
(g) a second electronic display for displaying systolic and diastolic pressures; and
(h) an electrical circuit connected to the pressure transducer and to the button for controlling said first and second display.

The first display, for displaying the instantaneous pressure in the air bladder, is a simulated mercury column. The electrical circuit provides an output of digital signals, representing the systolic and diastolic pressures, for use by a programmed digital computer for storage and processing. It also provides an output of manually or digitally entered patient identification data.

41 Claims, 12 Drawing Sheets

| FIG. 4aa | FIG. 4ab |
|---|---|

Interrupt Service for Systolic/Diastolic Button.

HYBRID SPHYGMOMANOMETER

CROSS-REFERENCE TO RELATED APPLICATION

The present application is a continuation-in-part of application Ser. No. 09/112,502, filed Jul. 9, 1998 and application Ser. No. 09/265,734, filed Mar. 10, 1999 both abandoned.

BACKGROUND OF THE INVENTION

The present invention relates to a sphygmomanometer; that is, a device for measuring blood pressure using the standard Korotkoff arm cuff. More particularly, the present invention concerns a blood pressure meter for use by a physician or trained operator which incorporates electronics to overcome the disadvantages of a conventional mechanical device.

Blood pressure measurement is a standard part of any medical examination; in fact, it is the most common reason for visiting a doctor. The basic process involves two components: one is the measurement of the pressure of a cuff encircling the arm; the other is the estimation of the blood pressure based on the detection of sounds or oscillations as the cuff is gradually deflated. The standard technique, against which all others are compared, uses a mercury sphygmomanometer and a stethoscope, with a trained operator listening for Korotkoff sounds. In this case, the cuff pressure is measured by the mercury column, and the operator estimates the blood pressure from this column by the appearance and disappearance of the Korotkoff sounds.

While this technique is accepted as the "gold standard" of blood pressure measurement, it is subject to avoidable errors such as operator bias (the tendency of the operator to over or under estimate the blood pressure as the mercury column falls), excessively rapid deflation of the cuff, and digit preference (the excessive use of five's or zero's for the terminal digits).

A variant of the mercury sphygmomanometer is the aneroid device, in which the mercury column is replaced by a pressure gauge with a dial. The accuracy of these devices is questionable, however, because it is not possible to calibrate the gauge and the dial is relatively difficult to read as compared to a linear mercury column. Furthermore, the accuracy of the pressure gauge may change over time.

An increasing number of electronic devices is available in which the cuff pressure is detected by an electronic transducer and the blood pressure is derived, either from the oscillations of pressure within the cuff (the oscillometric method) or from electronic detection of the Korotkoff sounds (the auscultatory method). In both cases, the blood pressure is estimated using some electronic algorithm rather than by direct observation. The accuracy of such electronic devices varies greatly, even though they are calibrated against a mercury sphygmomanometer. The cause of the inaccuracies is not the measurement of the cuff pressure, but the algorithm used to estimate blood pressure.

It is desirable, therefore, to retain the involvement of the trained operator in blood pressure measurement. One such "hybrid" electronic blood pressure measuring device is disclosed in the U.S. Pat. No. 5,201,320. This device incorporates an electronic transducer for measuring the cuff pressure in addition to the conventional mercury pressure column. The primary use of the mercury column is the calibration of the pressure transducer and the electronic control and display circuitry. The device regulates the release of air from the cuff using an electronically controlled solenoid outlet valve. The operator presses a button when he/she hears the systolic and diastolic pressures, and the pressure values are displayed on two LED displays. This system has the advantage of utilizing the expertise of the operator in identifying the Korotkoff sounds while eliminating some of the operator bias or error in identifying the systolic and diastolic pressures. This system has the disadvantage of lacking accurate control of the cuff deflation so that the rate of deflation is not a constant. This impairs the accuracy of the correction for reaction time of the operator.

The U.S. Pat. No. 5,464,017 discloses a blood pressure meter which eliminates entirely the mercury column for measuring pressure. As in the case of the '320 patent referred to above, this device uses an electronic transducer and displays the cuff pressure with an array of LED's. In particular, the device includes a first LED display for indicating whether the blood pressure values are increasing or decreasing and second and third LED displays for displaying the systolic and diastolic blood pressure values, respectively. A physician/operator closes a switch on hearing the Korotkoff sounds which denote systolic and diastolic pressures. This signal is transmitted via an infrared or high frequency signal to a receiver, amplified and then supplied as an interrupt signal to a microprocessor to latch the blood pressure values.

This device has the advantage of eliminating the use of mercury in measuring pressure. Mercury is highly toxic and has, in fact, been banned in several European countries on environmental grounds. However, the transmitter/receiver arrangement for signaling the Korotkoff sounds is unnecessarily complicated and expensive and the LED display does not convey to the operator, in an easy-to-read way, the same pressure information as a mercury column.

SUMMARY OF THE INVENTION

It is a principal object of the present invention to provide a "hybrid" sphygmomanometer which combines the advantages of the mercury sphygmomanometer and an electronic device.

A more particular object of the present invention is to provide a blood pressure measurement device which relies on a trained operator to detect Korotkoff sounds.

It is a further particular object of the present invention to provide a blood pressure measurement device which is easy to use.

It is a further particular object of the present invention to provide a blood pressure measurement device which is inexpensive and accurate and which does not require calibration.

It is a further particular object of the present invention to provide a blood pressure measurement device having an improved system for control of cuff deflation.

It is a further particular object of the present invention to provide a blood pressure measurement device which has one or more electronic outputs for electronically downloading blood pressure measurements to a computer.

These objects, as well as other objects which will become apparent from the discussion that follows, are achieved, according to the present invention, by providing a sphygmomanometer which comprises:

(a) an arm cuff with an inflatable air bladder;

(b) a pumping device for inflating the air bladder;

(c) a manually and/or electrically actuated air outlet valve for deflating the air bladder;

(d) an air pressure transducer operative to receive the pressure in the air bladder and to produce an electrical signal representing this pressure;

(e) a manually operated switch for generating systolic and diastolic interrupt signals;

(f) a first electronic display for displaying the measured instantaneous pressure in the air bladder in the form of a bar graph;

(g) a second electronic display for displaying systolic and diastolic pressures; and (h) an electrical circuit, connected to the pressure transducer and to the switch, for controlling said first and second display.

According to one preferred feature of the present invention, the first display, for displaying the instantaneous pressure in the air bladder, is a simulated mercury column; i.e., a bar graph formed of an LED or LCD display or a display screen, such as a CRT or flat panel display.

The two displays are preferably implemented with either LCDs or LEDs. Advantageously, a linear, LED display may be used to implement the simulated mercury column.

According to another preferred feature of the present invention, the electrical circuit provides digital signals, representing the systolic and diastolic pressures, for use by a computer for storage and processing. These signals may be transmitted directly via a serial or parallel port, radio frequency transmission, or via a modem which converts the signals into tones for transmission over a conventional telephone line.

The pumping device for inflating the air bladder may be a conventional squeeze bulb, as is used in conventional mercury sphygmomanometers, or an electrically operated pump.

The electrical circuit preferably includes a microprocessor which is capable of determining the pulse rate from the periodic changes in the blood pressure. This pulse rate is preferably displayed using a third LCD or LED display. The microprocessor preferably also determines when the pressure in the cuff air bladder is reduced at a rate faster than a predetermined rate, and signals a warning, through a warning light, that the cuff deflation is too rapid.

The air outlet valve of the blood pressure measurement device may comprise a conventional, mechanically-actuated valve or an electrically actuated valve, or both. In one preferred embodiment, the system is configured so that the cuff can be deflated by manually twisting a valve knob, or by pressing a knob or button with the thumb, and then manually signaling the Korotkoff sounds by pressing another button or pulling a trigger operated by the forefinger. The latter button or trigger directly actuates an electrical contact or switch which signals the device, when first actuated, that systolic pressure is present and, when actuated a second time, that diastolic pressure is present.

The sphygmomanometer according to the invention may thus be operated in a manner which is virtually identical to that of the conventional mechanical devices known in the art. The only difference is that the operator must manipulate the manually operated button or trigger when he/she hears the Korotkoff sounds through a stethoscope. By operating this button or trigger the operator signals the electrical circuit to cause the systolic and diastolic pressures to be displayed on the second electronic display.

Deflation of the inflatable air bladder in the arm cuff may be effected by the operator in the conventional way by manually turning a deflation knob to open an air outlet needle valve by a prescribed amount. The rate of deflation is controlled by rotating the knob a small amount (for slow, steady deflation during the blood pressure measurement) or a larger amount (for rapid deflation when the blood pressure measurement has been completed). Alternatively, two buttons may be provided for actuation by hand: a first button which opens a "slow deflation" air valve, and a second button which opens a "rapid deflation" air valve. The slow deflation air valve allows a constant flow of air to escape so that the cuff pressure reduces substantially at a constant rate in the range of 2 mm to 3 mm Hg per second.

Since one hand of the operator must be used to hold the sound receiving element of the stethoscope, only one hand is available for controlling the sphygmomanometer. To improve the ergonomics of this blood pressure measurement system, some other manual or electronic control of the cuff deflation may be provided. As noted above, a mechanically actuated air control valve may be used to deflate the cuff air bladder either slowly, or rapidly, or both. Alternatively, an electronic control may be provided to automatically deflate the cuff at a prescribed, desired rate, such as a rate in the range of 2 mm to 3 mm Hg per second, along with either a manual or electronic rapid deflation control.

According to a preferred embodiment of the invention, the electronic control includes a closed loop feedback circuit for adjusting an electro-mechanical air outlet valve in dependence upon the instantaneous cuff pressure. This electronic control accurately maintains a preset deflation rate in the range of 2 mm to 3 mm Hg per second and has the ability to produce a more rapid deflation rate at the press of a button.

If a microprocessor is provided, it may also be used to adjust for the reaction time of the human operator in determining the systolic and diastolic pressures. In particular, this microprocessor may be programmed to determine the reaction time of the operator during a calibration procedure, and thereafter to allow for this reaction time in determining the instant in which the systolic and diastolic pressures are latched.

According to a particular feature of the present invention, the microprocessor is provided with a correction algorithm to adjust the systolic and diastolic pressures. The correction algorithm adjusts the systolic pressure in accordance with the reaction time of the human operator when the systolic/diastolic switch is closed (by pressing a button or pulling a trigger) for the first time; the correction algorithm sets the diastolic pressure to the cuff pressure measured at the previous heartbeat when the switch is closed for the second time.

According to a particular feature of the present invention, either the measured systolic pressure or measured diastolic pressure or both, are displayed on the first (bar graph) display by indicating a small portion or segment of a bar at the position along the bar graph representing the systolic or diastolic pressure, respectively.

According to still another particular feature of the present invention, if the operator closes the switch twice in rapid succession, the reading will be aborted.

Finally, the sphygmomanometer according to the invention advantageously includes a keypad (which may be a touch screen LCD) or other input device such as a barcode reader or magnetic card scanner for supplying information to the microprocessor. This information may include, inter alia, the identification of each separate patient for whom the blood pressure is measured. In this way, a patient identification signal may be provided at the digital output of the microprocessor along with the systolic and diastolic pressures of that patient.

For a full understanding of the present invention, reference should now be made to the following detailed description of the preferred embodiments of the invention as illustrated in the accompanying drawings.

BRIEF DESCRIPTION OF THE DRAWINGS

FIG. 6, comprised of FIGS. 6a, 6b and 6c, is a flow chart showing the reaction time correction algorithm utilized in the sphygmomanometer of FIGS. 1–4.

DESCRIPTION OF THE PREFERRED EMBODIMENTS

The preferred embodiments of the present invention will now be described with reference to FIGS. 1–8 of the drawings. Identical elements in the various figures are identified with the same reference numerals.

Figure 1:
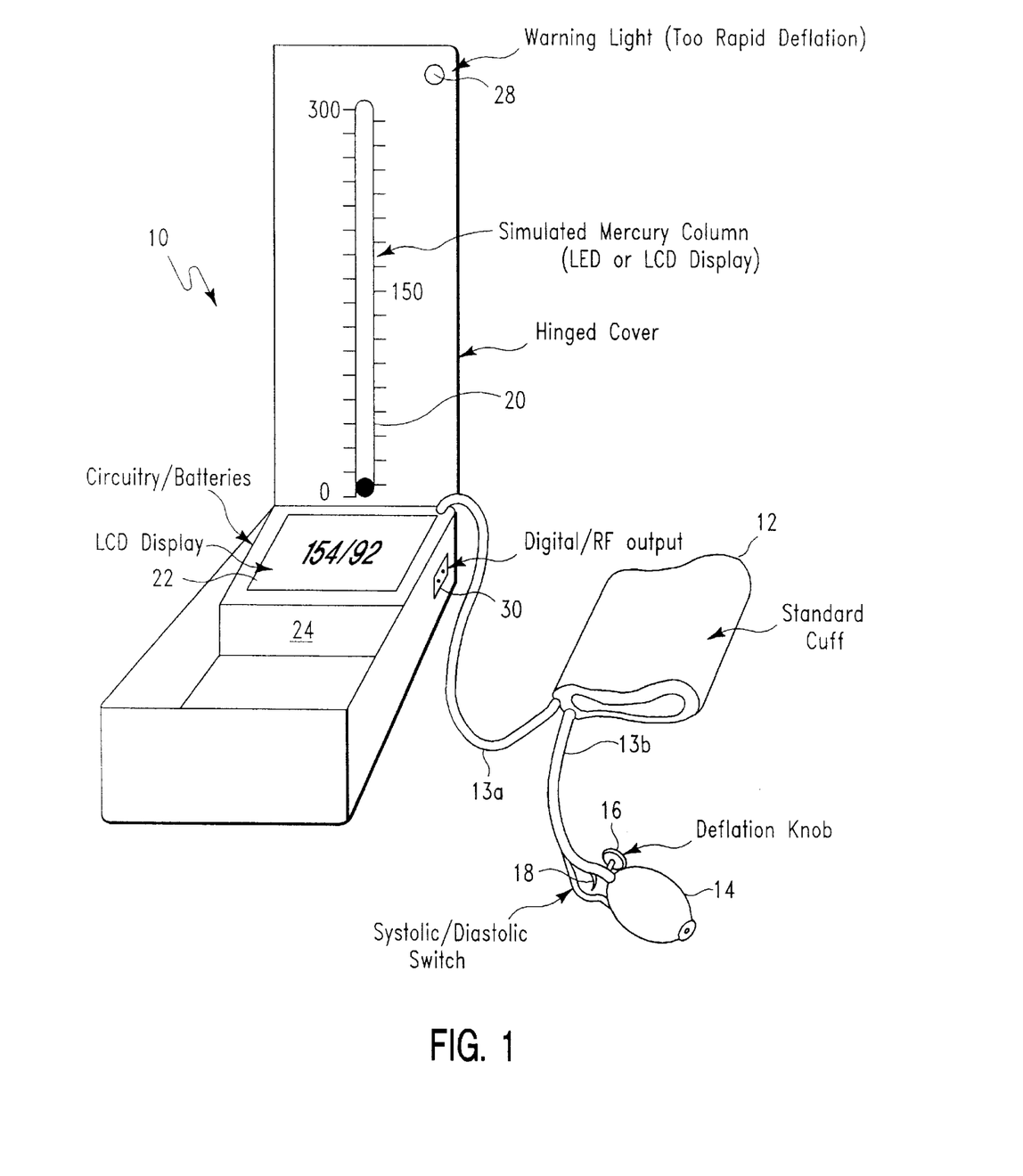
FIG. 1 is a perspective view of a hybrid sphygmomanometer according to the present invention which incorporates a simulated mercury column as well as a separate display for systolic and diastolic pressures.

FIG. 1 illustrates the principal features of the hybrid sphygmomanometer according to the present invention. This blood pressure measuring device 10 comprises a standard arm cuff with an inflatable air bladder 12; pressure tubes 13a and 13b; a squeeze bulb 14 for inflating the air bladder; an air outlet valve with a control knob 16 for deflating the air bladder; a manually operable button or trigger 18 for generating systolic and diastolic interrupt signals; a first electronic display 20 (preferably of LED's) for displaying the measured instantaneous pressure in the air bladder in bar graph format; a second electronic display 22 (preferably of LCD's) for displaying both systolic and diastolic pressures, as well as pulse rate, in digital format; and an electrical or electronic circuit, powered by batteries, arranged within a box-like housing 24. In addition, the device includes a warning light 28, indicating to the operator that the cuff is being deflated too rapidly, and a digital or RF output or plug 30 for downloading patient and blood pressure information to a computer. Finally, the device may be provided with an on/off switch (not shown). An alternative arrangement would be to have the device activated by the manual inflation of the cuff, and to switch itself off two minutes after the last reading is taken.

The sphygmomanometer according to the invention is operated in a very similar manner to a conventional, mercury sphygmomanometer. By pressing the trigger 18 upon hearing the Korotkoff sounds, the operator sends a signal to the electric circuit which then displays the systolic and diastolic pressures on the second (digital) display device 22.

As is customary, the operator may observe the instantaneous pressure of the air bladder within the arm cuff by observing the first (bar graph) display 20 which simulates a mercury column. If the air bladder is deflated too rapidly for the proper measurement of blood pressure, the operator is signaled by the warning light 28.

Finally, the device may be provided with a keypad (touch screen LCD), barcode reader, magnetic stripe reader, or other input device, so that the operator may enter the identification number of the patient whose blood pressure is being measured. The keypad may be built into the LCD display 22, as is well known in the art. The other input devices may be built into the box 24.

The electric circuitry within the device preferably includes a microprocessor (microcontroller) which is capable of storing the blood pressure values of a number of patients in association with the identification number of each patient. This information may then be downloaded to a programmed digital computer, under control of the keypad, for subsequent processing and storage.

For example, the computer may store a series of blood pressure measurements for each individual patient along with the date and time of each measurement to provide a historical record.

Figure 2:
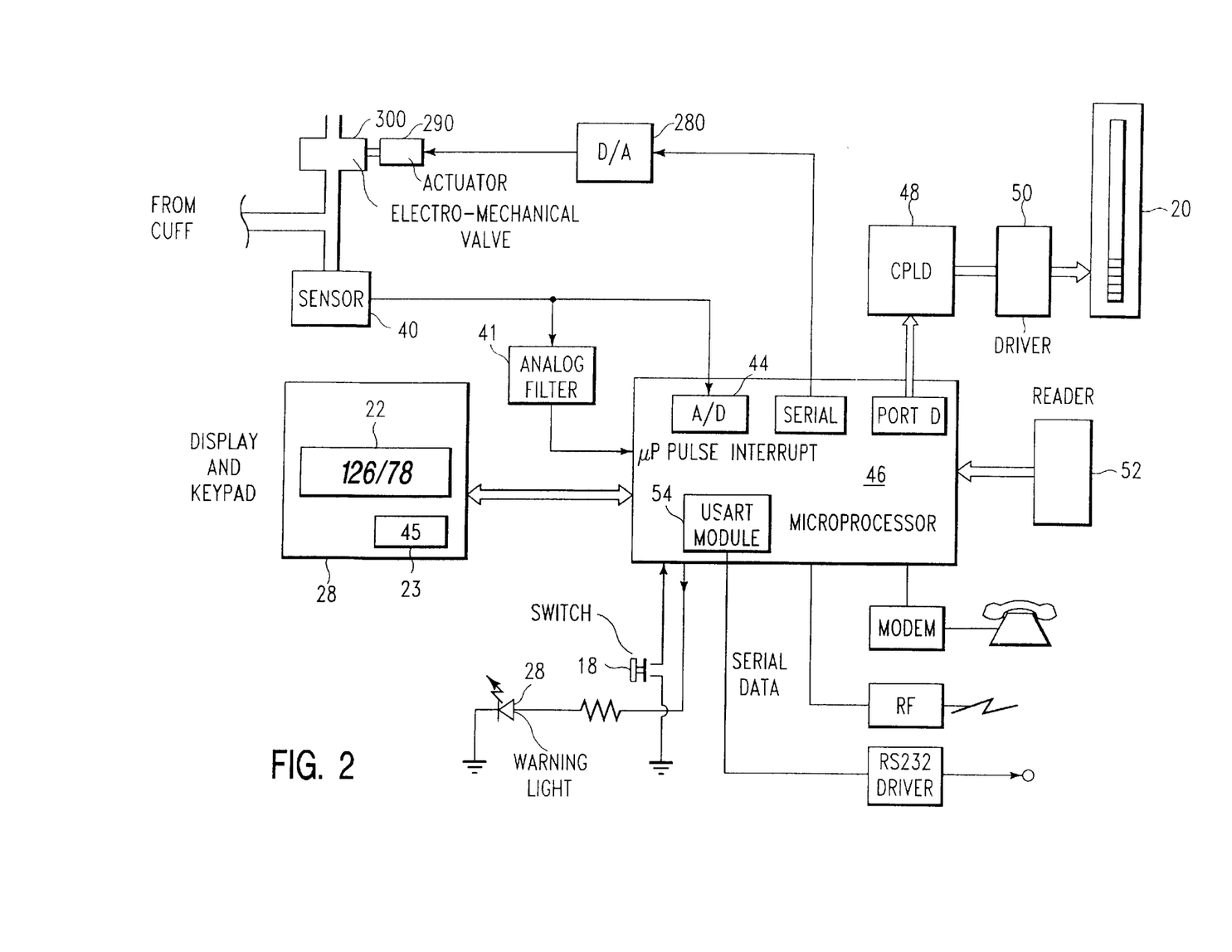
FIG. 2 is a block diagram of the electronic circuit incorporated in the sphygmomanometer of FIG. 1.
Figure 3:
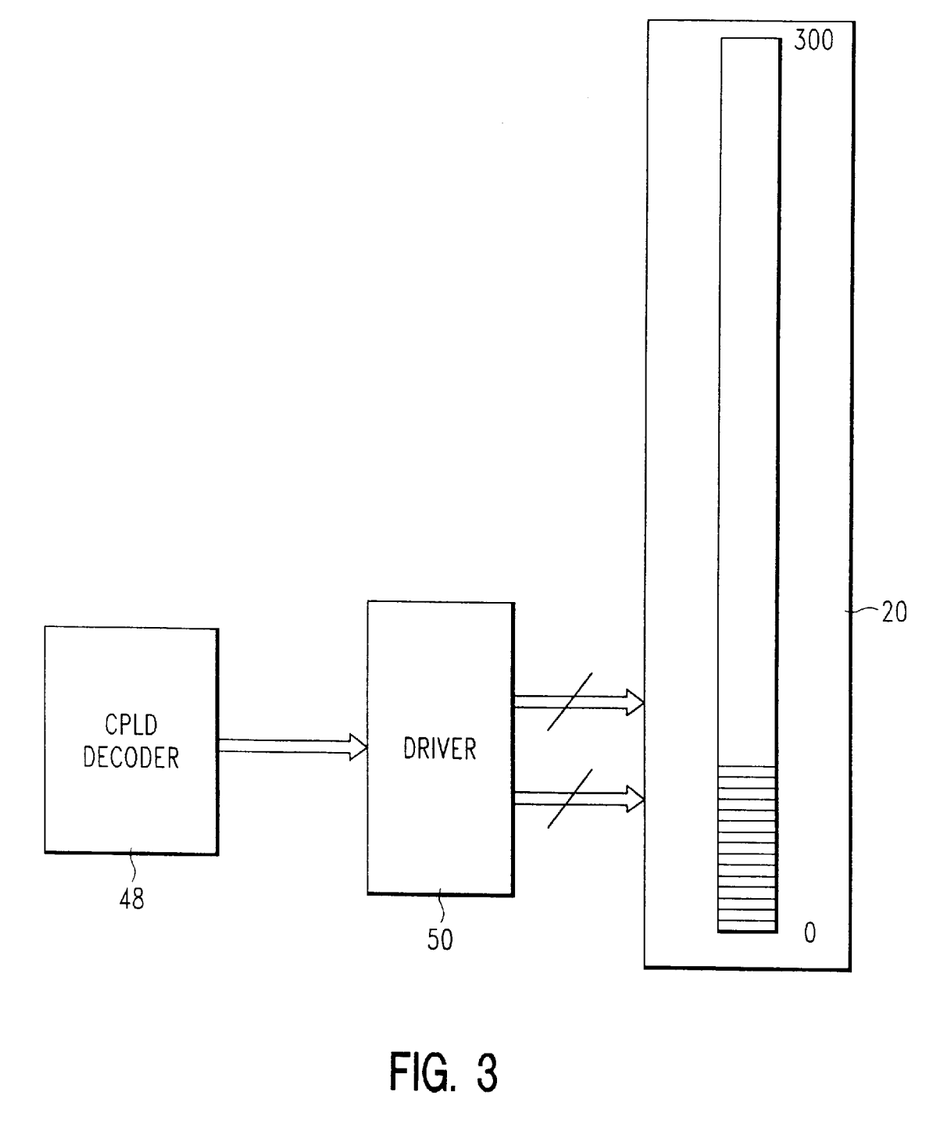
FIG. 3 is a block diagram showing a detail of the simulated mercury column used in FIG. 2.

FIGS. 2 and 3 illustrate the preferred embodiment of the electronic circuitry employed with the sphygmomanometer according to the invention. The air pressure within the air bladder, which is supplied to the circuitry via the tube 13a, is sensed by a pressure transducer 40 that produces an electrical signal representing blood pressure. This signal is internally signal conditioned, amplified and converted to a digital signal by an analog-to-digital converter 44 within a microprocessor 46. This pressure signal is also passed to an analog pulse filter 41 which generates a digital pulse upon variation of the blood pressure signal indicative of a heartbeat. This digital pulse is supplied as an interrupt signal to the microprocessor 46. The digital signal produced by the A/D converter is passed in parallel format as an input to the microprocessor 46 and to the simulated mercury column display 20.

The simulated mercury column display 20 may be a 100 or 150 element, LED or backlit LCD display. Each LED or LCD element represents a 2 or 3 mm portion of the mercury scale. The digital input signal is received by a decoder (complex programmable logic device or CPLD) 48 which drives the row or column transistor array 50. When a "1" appears at an output, the corresponding LED or LCD(s) in the display 20 is (are) activated. Only 100 or 150 of these outputs are used to indicate the presence or absence of mercury in the 0–300 mm range.

The microprocessor 46 also receives inputs from the systolic/diastolic switch 18 and a keypad 26. Other inputs which can provide a patient ID number, such as a bar code reader, magnetic stripe reader, fingerprint reader, or patient bracelet reader 52, may also be provided. The microprocessor generates the following outputs: the systolic/diastolic pressure display 22; the pulse rate display 23 (which may be indicated by the same digital readout devices as are used for the display 22); the warning light 28; and digital signals representing the systolic/diastolic pressure and pulse rate to the USART port 54, modem 56, and/or RF transmitter 58, respectively.

The microprocessor is programmed to receive and store patient identification information from the keypad in association with the systolic and diastolic pressures as well as the pulse rate of that patient. This information may be downloaded to a remote computer via the serial port 54, the modem 56 or the RF transmitter 58.

In a preferred embodiment of the invention, the microprocessor is a Microchip PIC 16C7X 8-bit CMOS microcontroller.

Figure 6A:
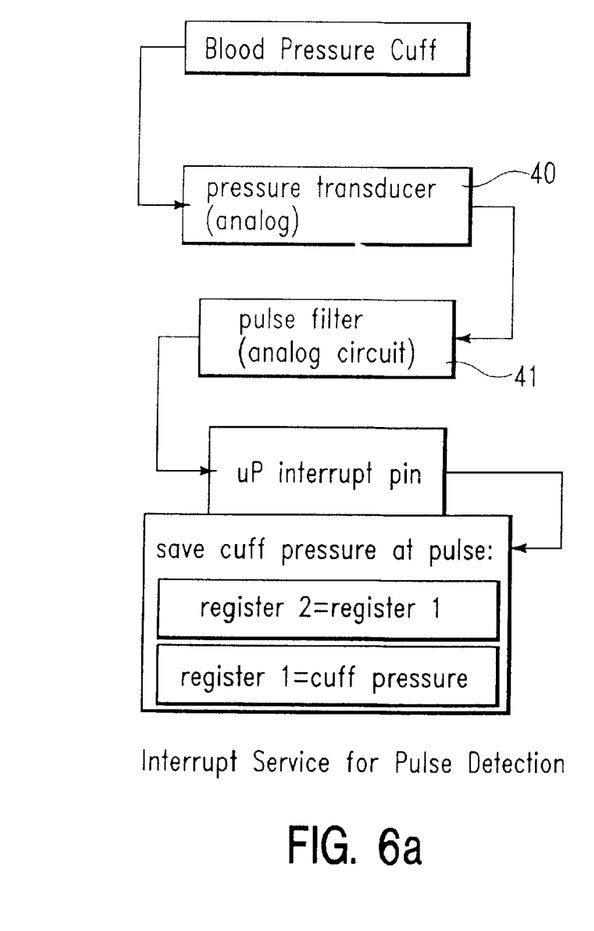
Figure 6B:
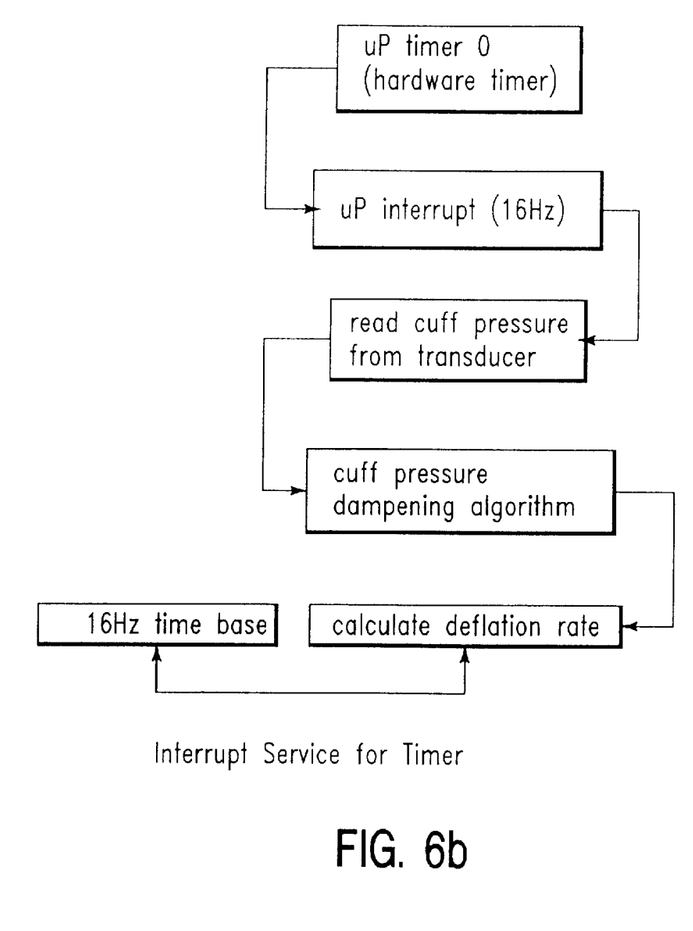
Figure 6C:
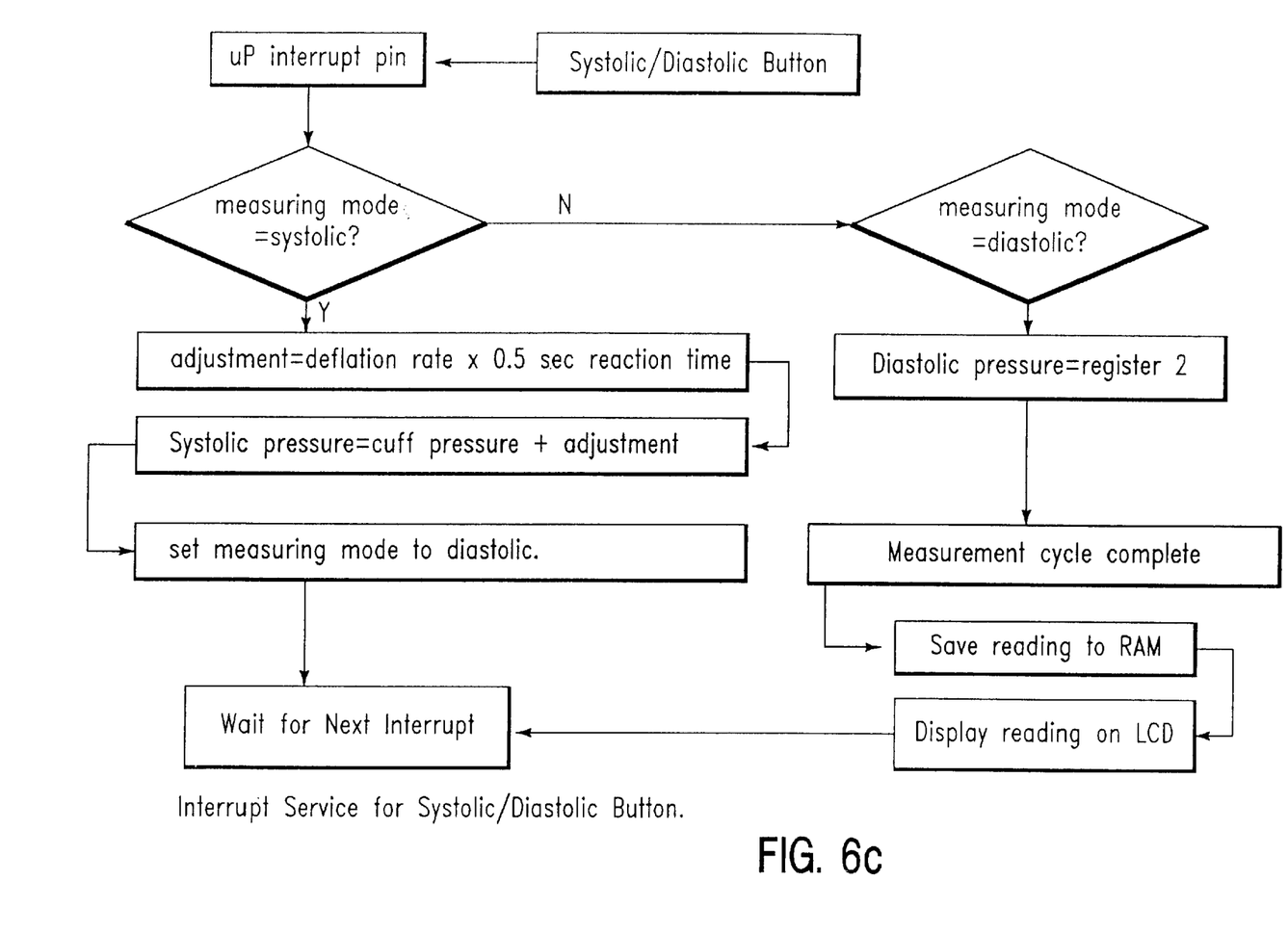
Figure 7:
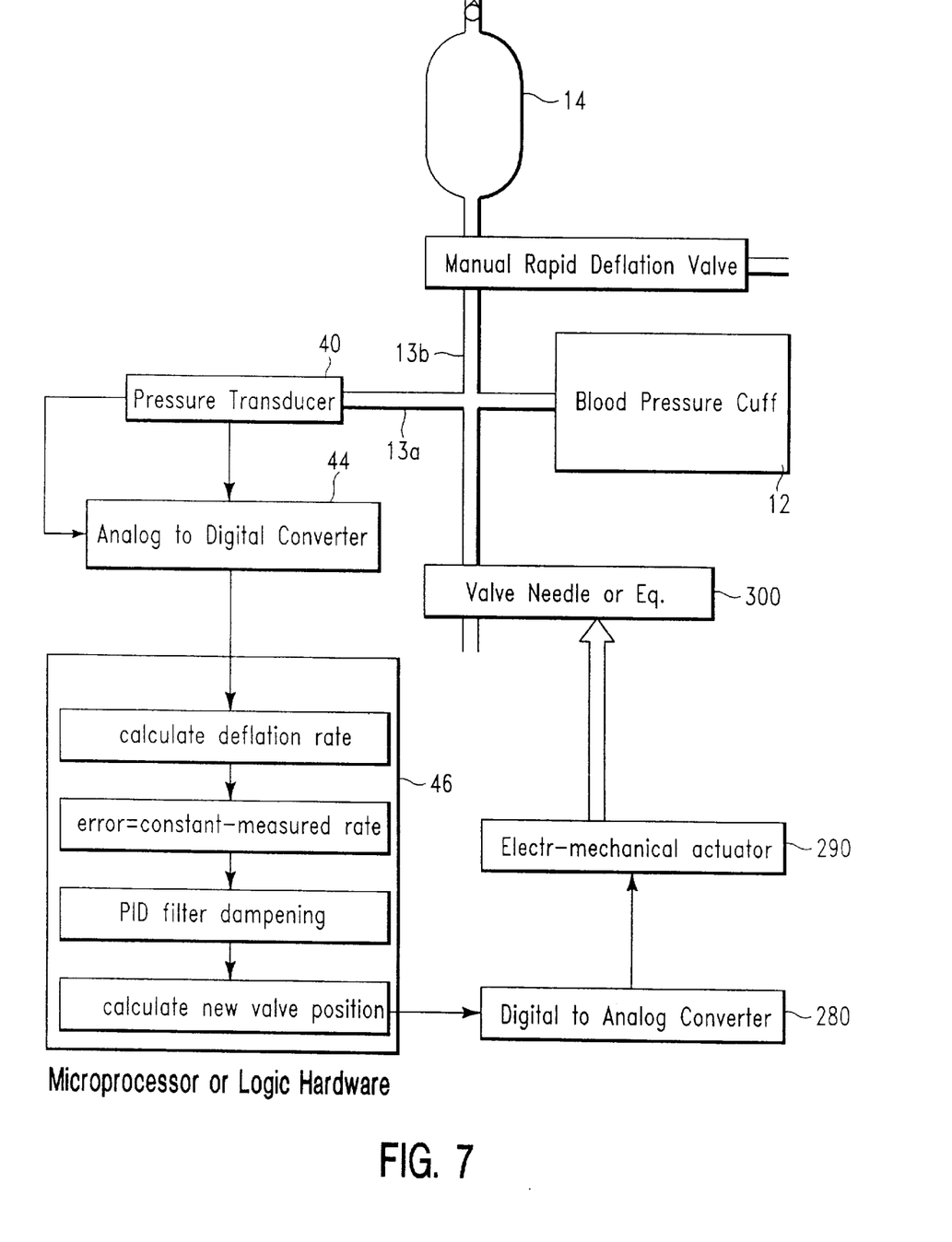
FIG. 7 is a block diagram illustrating the closed loop control system for deflation of the blood pressure cuff in the sphygmomanometer of FIGS. 1–4.
Figure 8:
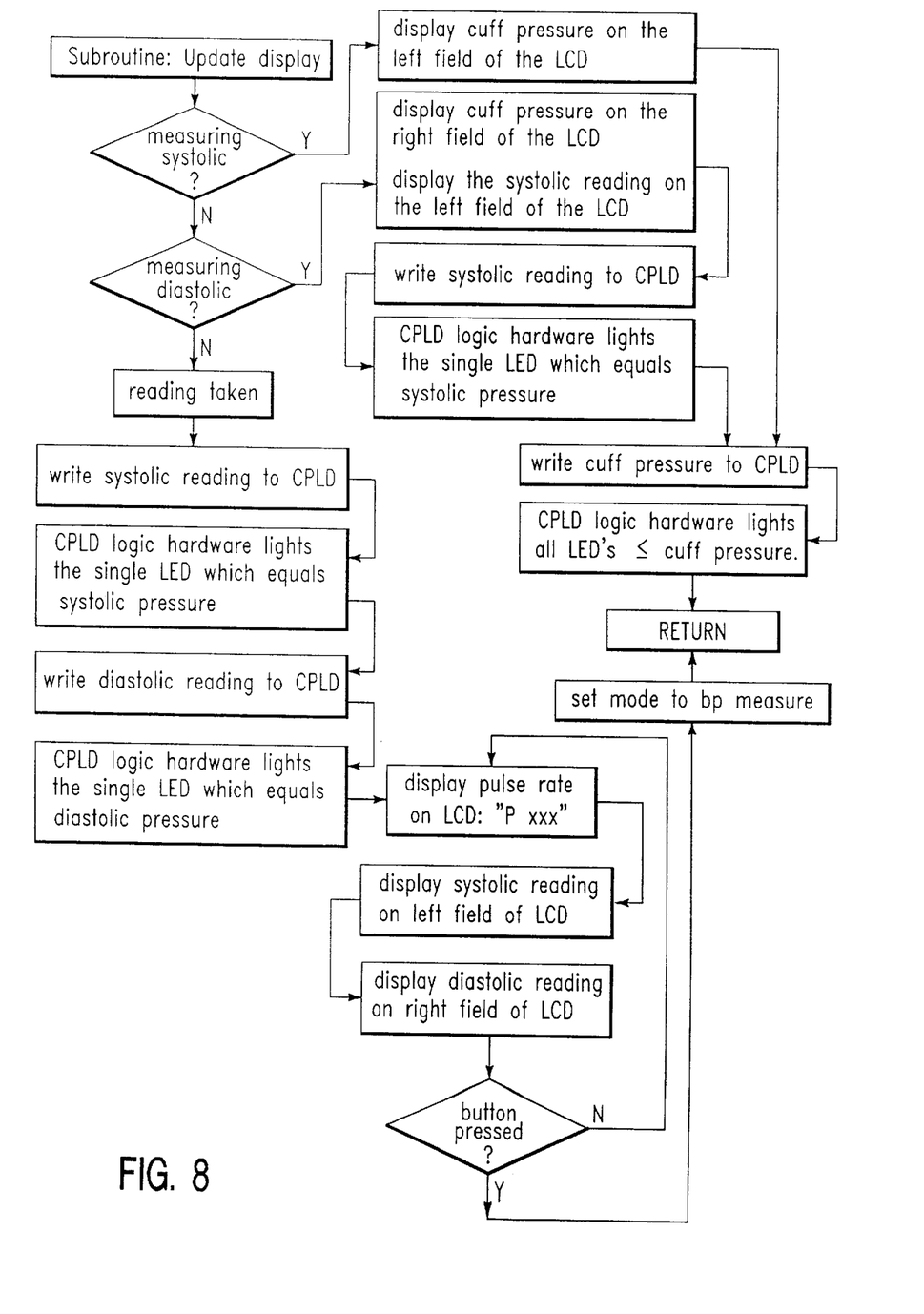
FIG. 8 is a flow chart of the subroutine "Update Display" employed in the operation program of FIG. 4.

The firmware operation of the microprocessor 46 is illustrated in the flowcharts of FIGS. 4a and 4b, FIGS. 6a, 6b and 6c, as well as FIGS. 7 and 8.

Figures 4, 4A:
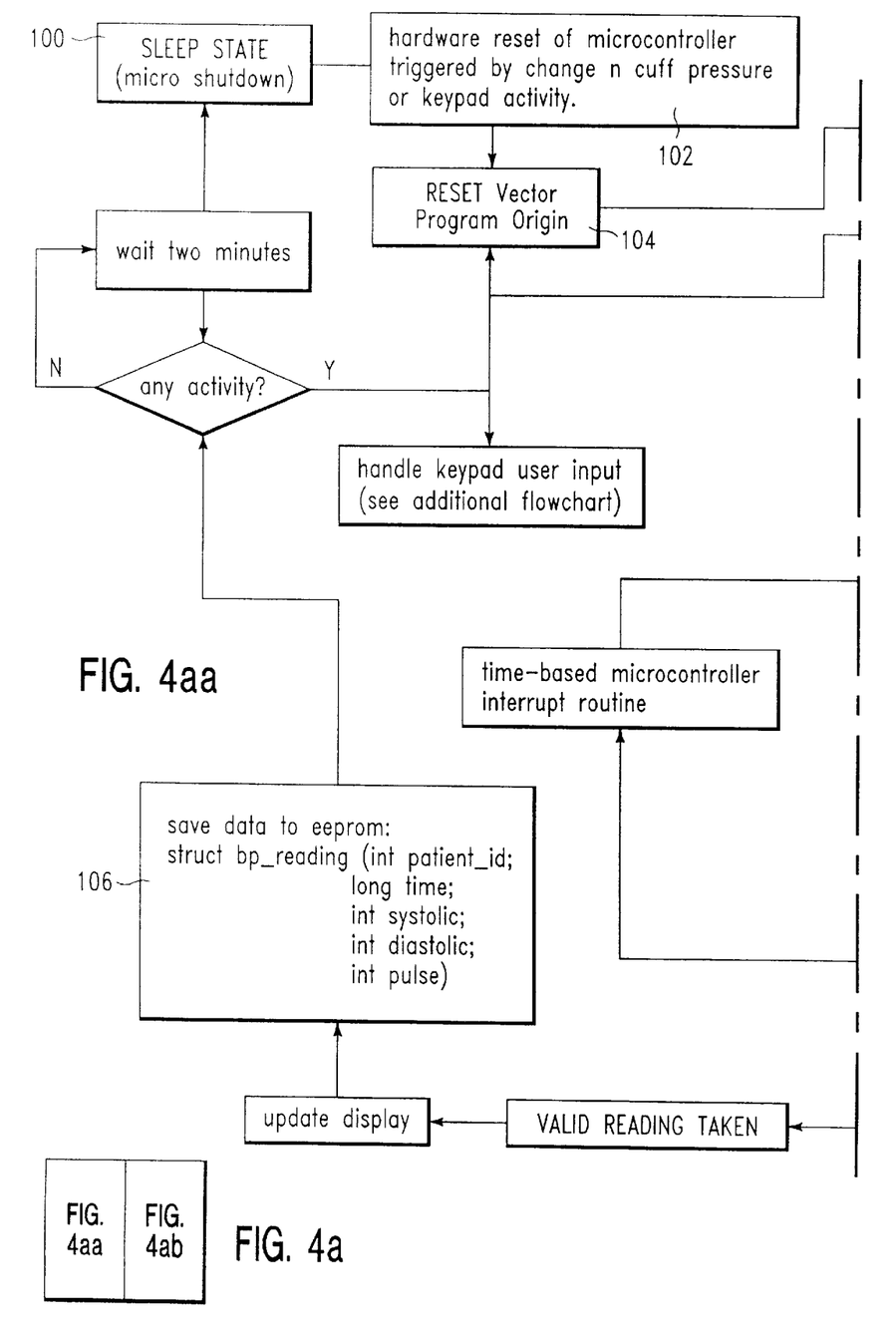
Figure 4:
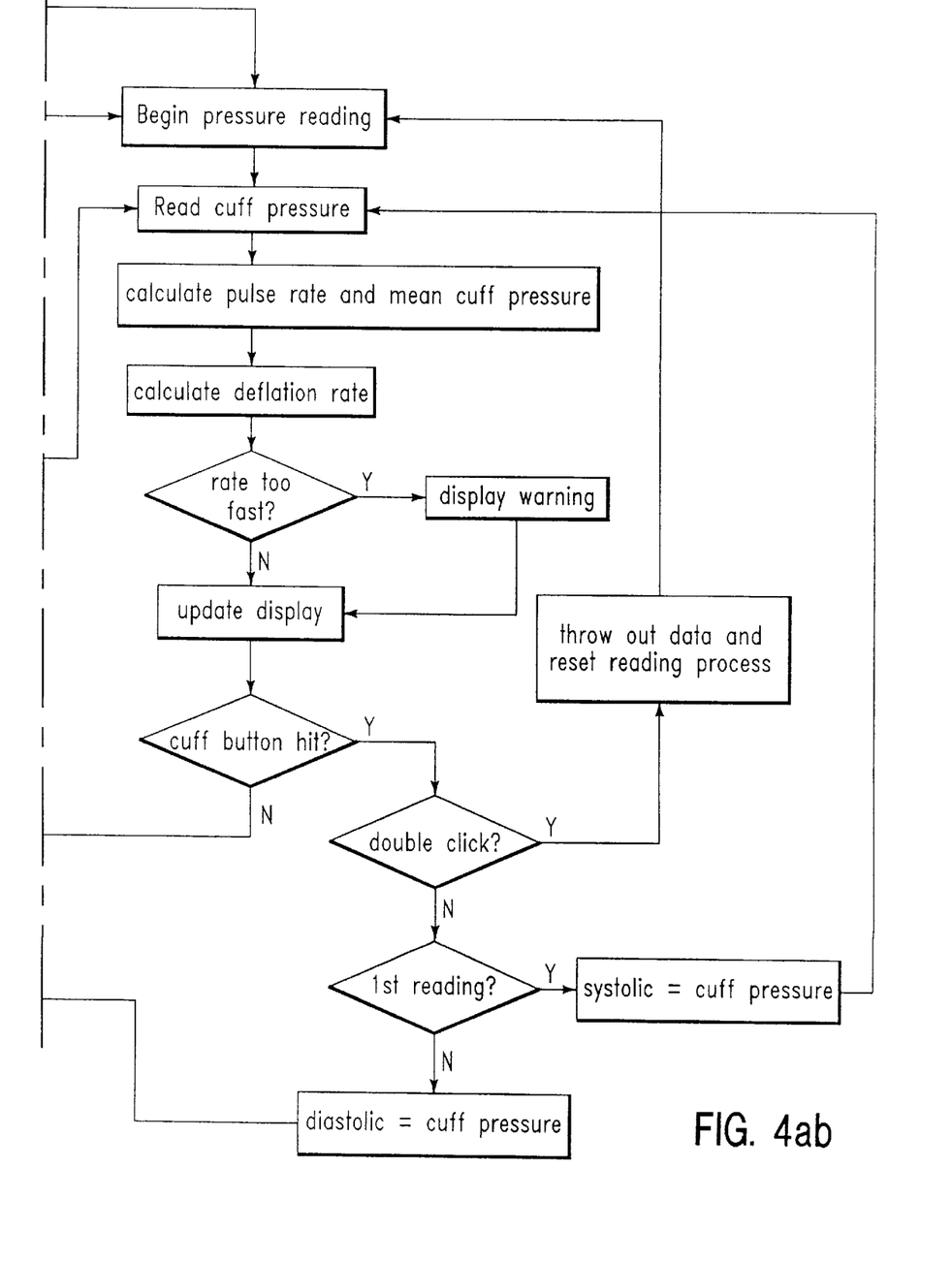
FIG. 4, comprised of FIGS. 4a and 4b, is a flow-chart of the operation of the sphygmomanometer of FIGS. 1–3.
Figures 4, 4B:
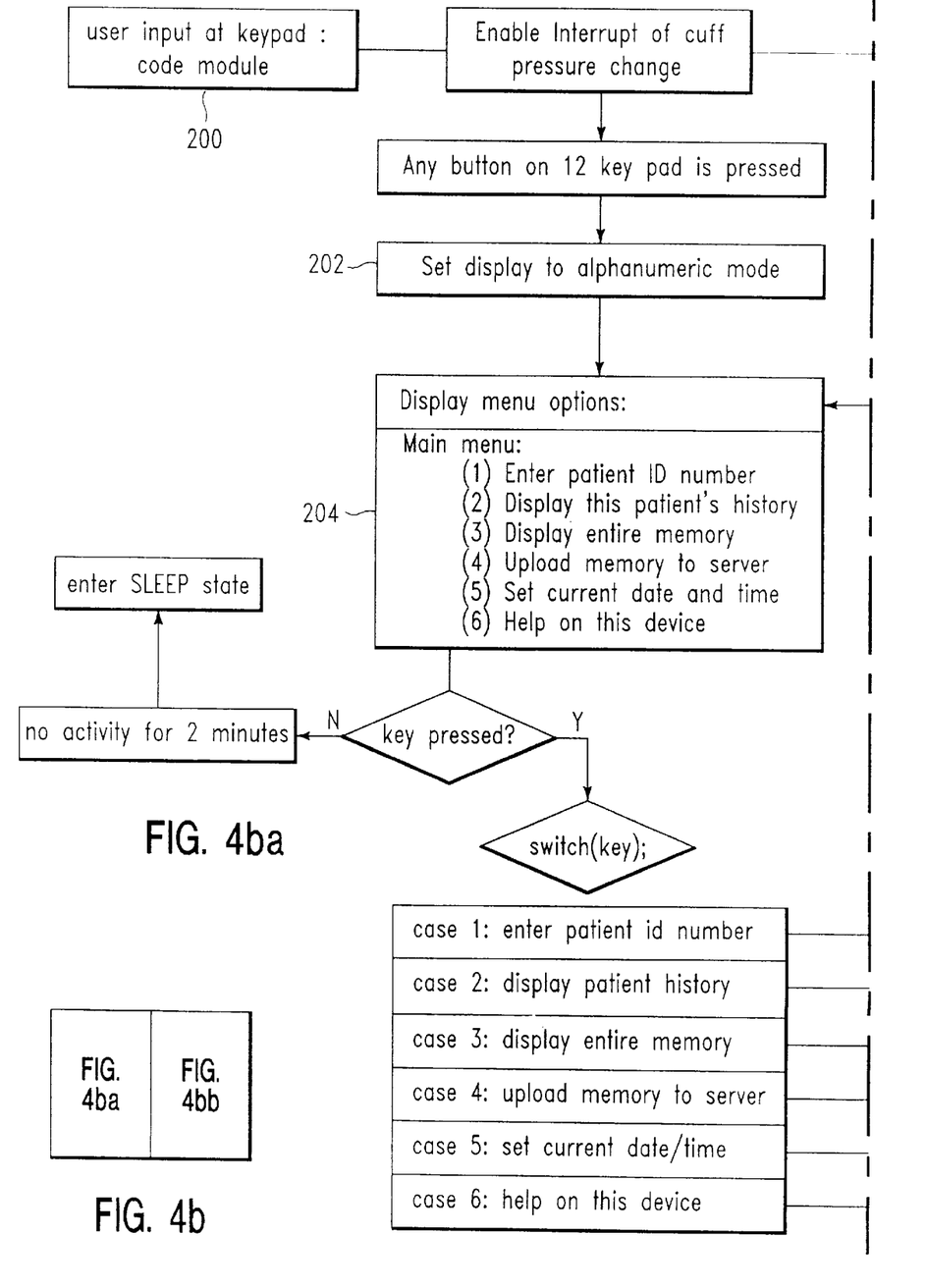

FIG. 4a shows the operation during a blood pressure measurement; FIG. 4b shows the operation of the microprocessor in response to keypad entries. In FIG. 4a, the microprocessor remains in a sleep state 100 until a change in cuff pressure or keypad activity is sensed 102. Thereafter, the operational vectors are reset 104 and the blood pressure readings are taken and displayed 106. The subroutine for the block "Update Display" is illustrated in FIG. 8 and described hereinbelow. If there is no activity for a period of two minutes, the microprocessor enters the sleep state again.

In FIG. 4b, the microprocessor senses a keypad entry 200, the display is set to the alphanumeric mode 202, and the menu options are displayed 204. Thereafter, the microprocessor response to the menu option selected (case 1–case 6) and carries out the respective function. If no key is pressed for a period of two minutes, the microprocessor enters the sleep state again.

Figure 5:
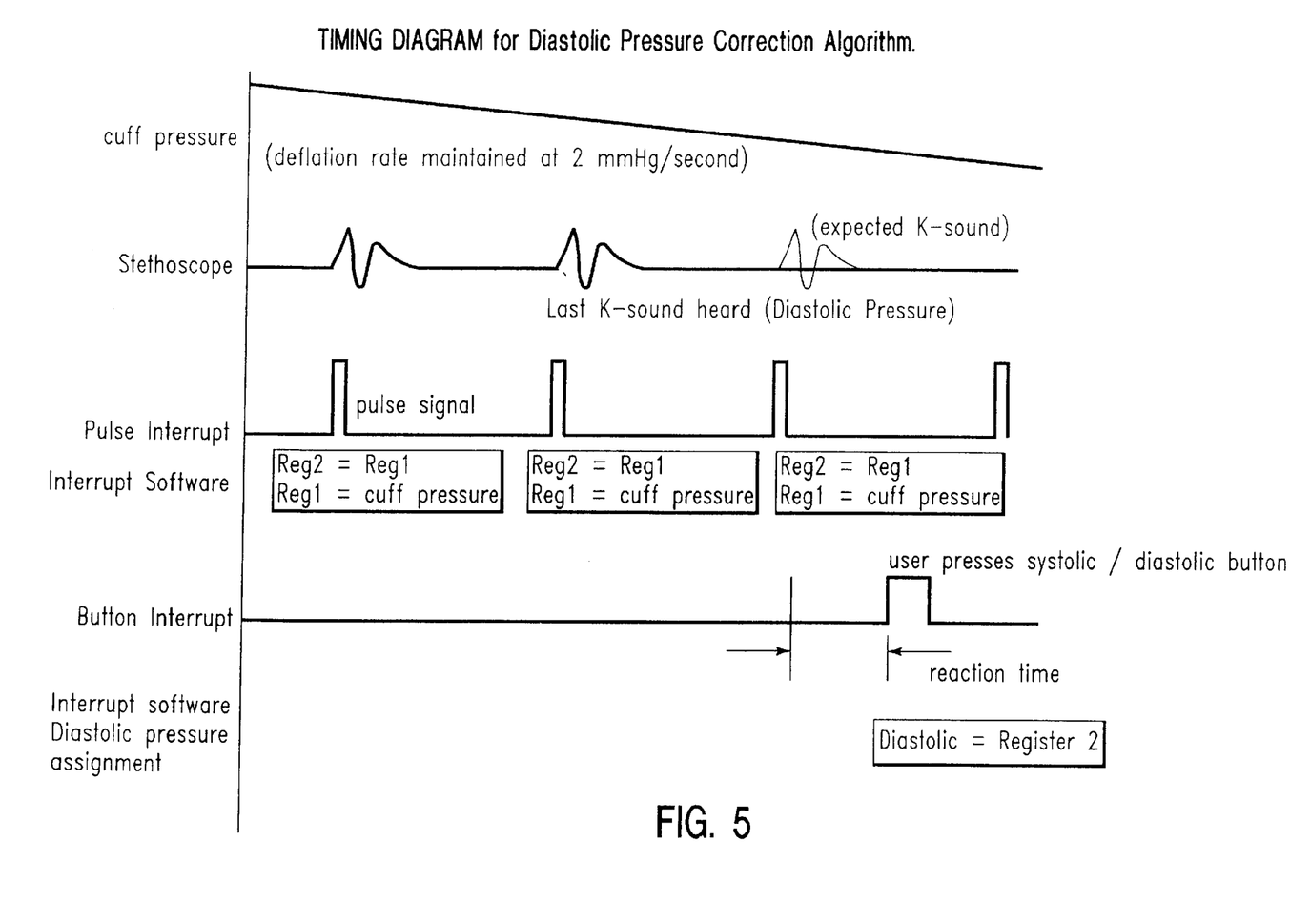
FIG. 5 is a timing diagram illustrating the calibration procedure of the sphygmomanometer of FIGS. 1–4.

To correct for the delay in closing the systolic/diastolic switch due to the reaction time of the operator, the microprocessor first runs through a calibration cycle to measure the reaction time of this operator. FIG. 5 is a time diagram which illustrates this process. The first line of the diagram shows the steadily reducing cuff pressure. The rate of deflation must be substantially constant for this system to accurately determine reaction time in the first instance and subsequently to accurately determine the systolic and diastolic pressures.

The next line on the time diagram illustrates the acoustic signal heard by the operator through the stethoscope. Illustrated are two Korotkoff sounds representative of diastolic pressure. As these signals occur, the pressure transducer 40 picks up a slight variation in pressure. This variation is filtered through an analog pulse filter 41 (shown in FIG. 2) and the pulse output of the device 41 (shown on the third line of FIG. 5) is supplied to an interrupt pin of the microprocessor 46 (shown also in FIG. 6a). When this occurs, the previous contents of register 1 are stored in register 2 and the new cuff pressure is stored in register 1. This operation is repeated upon receipt of each pulse interrupt signal.

Thereafter, whenever the operator closes the systolic/diastolic switch (by pressing a button or pulling a trigger) to indicate systolic or diastolic pressure, the contents of register 2 are supplied to the systolic/diastolic display 22 (FIG. 6c).

FIG. 6b shows that the time base, that is used to calculate the deflation rate, is provided by an internal hardware timer within the microprocessor which generates an interrupt at a programmed frequency. This interrupt is also used to provide a sampling frequency for reading the pressure in the cuff. In the preferred embodiment of the invention, the transducer is sampled 16 times per second. This sampling frequency may be increased to provide a finer resolution for calculating the rate of deflation.

The cuff pressure dampening algorithm maintains a stack which holds the past eight samples from the transducer. At each sampling period, the cuff pressure value returned from the sampling routine is the running average of the stack. This algorithm dampens the readings slightly and gives the simulated mercury column display a more realistic and "heavy" feel. It is part of the correction algorithm because it serves to dampen the sudden increase in cuff pressure at the systole.

As noted above, it is important for accuracy that the cuff pressure be reduced at a substantially constant rate (deflation rate). Preferably, this rate is in the range of 2 mm to 3 mm Hg per second. FIG. 7 illustrates a closed loop system for reducing the error in deflation rate to substantially zero.

FIG. 7 shows the blood pressure cuff 12 and the squeeze bulb 14 connected via the flexible tube 13b. A further flexible air tube 13a connects the blood pressure cuff to the pressure transducer or sensor 40. The output of the pressure transducer is passed through the A/D converter 44 to the microprocessor 46 which calculates (1) the actual deflation rate and (2) the difference between the actual and the desired deflation rate (error), which is preferably in the range of 2 mm to 3 mm Hg per second. This error is passed through a proportional integral differential (PID) filter, to avoid overcompensation and ringing, and the output is used to calculate a new position of an air outlet valve. This valve position is passed through a D/A converter 280 to an electromechanical actuator 290 for the valve 300.

In a preferred embodiment of the invention, the pressure transducer 40 is a Motorola MPX 5050 GP temperature stabilized pressure sensor, and the outlet valve 300 is a pogo pin pneumatic valve manufactured by TiNi Alloy Company, 1621 Neptune Drive, San Leandro, Calif. 94577.

FIG. 8 is a flow chart for the subroutine "Update Display" which is used in the operational program shown in FIG. 4a.

The software incorporates a resettable mode switch indicating whether systolic or diastolic readings are being taken. This mode switch has three states: a first state in which the systolic pressure is being measured; a second state, triggered by the first time the systolic/diastolic switch is closed, indicating that diastolic pressure is being measured, and a third state, triggered by the second close of the systolic/diastolic switch, indicating that the diastolic pressure has been reached.

The subroutine tests this mode switch. If systolic pressure is being measured, the measured instantaneous cuff pressure is displayed in the left field of the systolic/diastolic LCD display 22 and the LED bar graph display 20.

After the systolic/diastolic switch has been closed for the first time, the decision block "measuring systolic?" will follow the N path to the "measuring diastolic?" decision block. Initially, the systolic reading will be displayed on the left field of the LCD display and the measured instantaneous cuff pressure will appear on the right field of the LCD display. Thereafter, the systolic reading will be passed to the bar graph display 20 and the single LED which equals the systolic pressure will be illuminated there. Finally, the measured instantaneous cuff pressure will also be passed to the bar graph display 20 and all of the LED's representing either the cuff pressure or a pressure less than the cuff pressure will be illuminated.

After the systolic/diastolic switch has been closed the second time, the decision block "measuring diastolic?" will take the N path downward and both readings, systolic and diastolic, will be displayed on both displays 20 and 22. Initially, both the systolic reading and the diastolic reading will be displayed on the bar graph display 20 by illuminating the single, individual LED's representing the systolic and diastolic pressures on the bar graph. Thereafter, the pulse rate will be displayed on the LCD display 22 as "P xxx". Finally, both the systolic reading and the diastolic reading will be displayed on the left and right fields of the LCD display 22, respectively.

The pulse rate is measured and constantly updated and stored by the microprocessor 46 by measuring the time between interrupt pulses received from the analog filter 41 (FIG. 2).

This condition will remain until the systolic/diastolic switch is closed for a third time and the system is reset to measure blood pressure again.

The hybrid sphygmomanometer according to the present invention has a number of advantages over the prior art. First, this blood pressure measurement device incorporates the same basic technique and accuracy of the mercury sphygmomanometer, without requiring mercury. Second, and perhaps most importantly, this device should be readily acceptable to medical professionals who are accustomed to using mercury sphygmomanometers.

The sphygmomanometer according to the invention avoids some of the inaccuracies of conventional blood pressure measurement—in particular, the operator bias and digit preference—and corrects for the delay in registering the diastolic pressure. Furthermore, the device may be manufactured at comparable or less expense than both the mercury sphygmomanometers and the various electronic devices of the prior art.

The blood pressure readings and pulse rate are captured and stored in electronic form and may be downloaded to a programmed digital computer for detailed analysis.

There has thus been shown and described a novel hybrid sphygmomanometer which fulfills all the objectives and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. A sphygmomanometer comprising, in combination:
   (a) an arm cuff with an inflatable air bladder;
   (b) a pumping device for inflating the air bladder;
   (c) an air outlet valve for deflating the air bladder;
   (d) an air pressure transducer operative to receive the pressure in the air bladder and to produce an electrical signal representing said pressure;
   (e) a manually operated switch for generating systolic and diastolic interrupt signals;
   (f) a first electronic display for displaying said pressure in the air bladder in the form of a bar graph, said first display having a plurality of hatch marks and numbers showing the level of pressure to be indicated by the bar graph and simulating a mercury column pressure gauge as used in a mercury sphygmomanometer;
   (g) a second electronic display for displaying systolic and diastolic pressures; and
   (h) an electrical circuit, connected to said pressure transducer and to said switch, for controlling said first and second display.

2. The sphygmomanometer defined in claim 1, further comprising a digital signal output port, coupled to said electrical circuit, providing digital signals representing said systolic and diastolic pressures, for transmission to a digital computer for storage and processing.

3. The sphygmomanometer defined in claim 2, wherein said digital signal output includes a modem for transmitting said digital signals over a telephone line.

4. The sphygmomanometer defined in claim 2, wherein said digital signal output includes an RF transmitter for wireless transmission of said digital signals.

5. The sphygmomanometer defined in claim 2, further comprising an input device coupled to said electrical circuit, for producing an electrical signal representing the identification of each separate patient, whereby a patient identification signal may be provided at said digital output along with the systolic and diastolic pressures of the respective patient.

6. The sphygmomanometer defined in claim 5, wherein said input device is a keypad.

7. The sphygmomanometer defined in claim 5, wherein said input device is a fingerprint reader.

8. The sphygmomanometer defined in claim 5, wherein said input device is a barcode reader.

9. The sphygmomanometer defined in claim 5, wherein said input device is a magnetic stripe reader.

10. The sphygmomanometer defined in claim 1, wherein said first display is an LCD display.

11. The sphygmomanometer defined in claim 1, wherein said first display is an LED display.

12. The sphygmomanometer defined in claim 1, wherein said second display is a dual decimal number display.

13. The sphygmomanometer defined in claim 12, wherein said second display is an LCD display.

14. The sphygmomanometer defined in claim 12, wherein said second display is an LED display.

15. The sphygmomanometer defined in claim 1, wherein pumping device is a squeeze bulb.

16. The sphygmomanometer defined in claim 1, wherein said pumping device is an electrically operated pump.

17. The sphygmomanometer defined in claim 16, further comprising a third display connected to said processor means for displaying said pulse rate.

18. The sphygmomanometer defined in claim 1, wherein said electrical circuit includes processor means for determining pulse rate from said signal representing pressure.

19. The sphygmomanometer defined in claim 1, further comprising a further display connected to said electrical circuit for indicating when the pressure in said air bladder is reduced at a rate faster than a predetermined rate.

20. The sphygmomanometer defined in claim 1, wherein said air outlet valve is a mechanically actuated valve.

21. The sphygmomanometer defined in claim 1, wherein said air outlet valve is an electrically actuated valve.

22. The sphygmomanometer defined in claim 1, wherein said electrical circuit includes processor means for adjusting for the reaction time of a human operator in determining said systolic and diastolic pressures.

23. The sphygmomanometer defined in claim 22, wherein said processor means is responsive to a calibration to determine the reaction time of a human operator.

24. The sphygmomanometer defined in claim 1, wherein said first display includes a display screen.

25. The sphygmomanometer defined in claim 1, wherein the air outlet valve is manually controlled.

26. The sphygmomanometer defined in claim 1, wherein the air outlet valve is electrically controlled.

27. The sphygmomanometer defined in claim 26, wherein said air outlet valve is a proportional valve responsive to an analog signal, for controlling the rate of air flow in dependence upon the magnitude of said signal.

28. The sphygmomanometer defined in claim 26, wherein said electrical circuit further comprises electronic means for electrically controlling said outlet valve, said electronic means having a closed loop feedback circuit for adjusting the outlet valve in dependence upon said signal provided by said pressure transducer.

29. The sphygmomanometer defined in claim 27, wherein said electronic means is operative to deflate the air bladder at a substantially constant rate in the range of 2 mm to 3 mm Hg per second.

30. The sphygmomanometer defined in claim 1, wherein the measured systolic pressure is also displayed on said first display by indicating and maintaining the position along the bar graph representing said systolic pressure.

31. The sphygmomanometer defined in claim 1, wherein the measured diastolic pressure is also displayed on said first display by indicating and maintaining the position along the bar graph representing said diastolic pressure.

32. The sphygmomanometer defined in claim 1, wherein said first display is comprised of a plurality of bar graph segments, arranged in a line, and means for switching said segments on and off.

33. The sphygmomanometer defined in claim 32, wherein the measured systolic pressure is also displayed on said first display by indicating and maintaining the position along the bar graph representing said systolic pressure by causing one of said segments to remain illuminated.

34. The sphygmomanometer defined in claim 32, wherein the measured diastolic pressure is also displayed on said first display by indicating and maintaining the position along the bar graph representing said diastolic pressure by causing one of said segments to remain illuminated.

35. A sphygmomanometer comprising, in combination:
    (a) an arm cuff with an inflatable air bladder;
    (b) a pumping device for inflating the air bladder;
    (c) an air outlet valve for deflating the air bladder;
    (d) an air pressure transducer operative to receive the pressure in the air bladder and to produce an electrical signal representing said pressure;
    (e) a manually operated switch for generating systolic and diastolic interrupt signals;
    (f) an electronic display for displaying systolic and diastolic pressures;
    (g) an electrical circuit, connected to said pressure transducer and to said switch, for controlling said display; and
    (h) a further display connected to said electrical circuit for indicating when the pressure in said air bladder is reduced at a rate faster than a predetermined rate.

36. A sphygmomanometer comprising, in combination:
    (a) an arm cuff with an inflatable air bladder;
    (b) a pumping device for inflating the air bladder;
    (c) an air outlet valve for deflating the air bladder;
    (d) an air pressure transducer operative to receive the pressure in the air bladder and to produce an electrical signal representing said pressure;
    (e) a manually operated switch for generating systolic and diastolic interrupt signals;
    (f) an electronic display for displaying systolic and diastolic pressures; and
    (g) an electrical circuit, connected to said pressure transducer and to said switch, for controlling said display;
    wherein said electrical circuit includes processor means for adjusting for the reaction time of a human operator in determining said systolic and diastolic pressures.

37. The sphygmomanometer defined in claim 35, wherein said processor means is responsive to a calibration to determine the reaction time of a human operator.

38. A sphygmomanometer comprising, in combination:
    (a) an arm cuff with an inflatable air bladder;
    (b) a pumping device for inflating the air bladder;
    (c) an air outlet valve for deflating the air bladder;
    (d) an air pressure transducer operative to receive the pressure in the air bladder and to produce an electrical signal representing said pressure;
    (e) a manually operated switch for generating systolic and diastolic interrupt signals;
    (f) a first electronic display for displaying said pressure in the air bladder in the form of a bar graph;
    (g) a second electronic display for displaying systolic and diastolic pressures; and
    (h) an electrical circuit, connected to said pressure transducer and to said switch, for controlling said first and second display;
    wherein the measured systolic pressure is also displayed on said first display by indicating and maintaining the position along the bar graph representing said systolic pressure.

39. The sphygmomanometer defined in claim 38, wherein said first display is comprised of a plurality of bar graph segments, arranged in a line, and means for switching said segments on and off.

40. A sphygmomanometer comprising, in combination:
    (a) an arm cuff with an inflatable air bladder;
    (b) a pumping device for inflating the air bladder;
    (c) an air outlet valve for deflating the air bladder;
    (d) an air pressure transducer operative to receive the pressure in the air bladder and to produce an electrical signal representing said pressure;
    (e) a manually operated switch for generating systolic and diastolic interrupt signals;
    (f) a first electronic display for displaying said pressure in the air bladder in the form of a bar graph;
    (g) a second electronic display for displaying systolic and diastolic pressures; and
    (h) an electrical circuit, connected to said pressure transducer and to said switch, for controlling said first and second display;
    wherein the measured diastolic pressure is also displayed on said first display by indicating and maintaining the position along the bar graph representing said diastolic pressure.

41. The sphygmomanometer defined in claim 40, wherein said first display is comprised of a plurality of bar graph segments, arranged in a line, and means for switching said segments on and off.

* * * * *